United States Patent
Perez et al.

(10) Patent No.: US 8,511,311 B2
(45) Date of Patent: Aug. 20, 2013

(54) ENDOTRACHEAL TUBE WITH SUBGLOTTIC SECRETION SUCTION AND DETACHABLE SUCTION CONNECTION LINE

(75) Inventors: Jorge Jimenez Perez, Raleigh, NC (US); Gary James Roth, Wake Forest, NC (US); Daniel Patrick Dwyer, Raleigh, NC (US)

(73) Assignee: Teleflex Medical Incorporated, Research Triangle Park, NC (US)

( * ) Notice: Subject to any disclaimer, the term of this patent is extended or adjusted under 35 U.S.C. 154(b) by 130 days.

(21) Appl. No.: 13/093,083

(22) Filed: Apr. 25, 2011

(65) Prior Publication Data

US 2012/0097168 A1    Apr. 26, 2012

Related U.S. Application Data (60) Provisional application No. 61/327,857, filed on Apr. 26, 2010.

(51) Int. Cl.
| | | |
|---|---|---|
| *A62B 9/04* | (2006.01) | |
| *A61M 39/00* | (2006.01) | |
| *A61M 39/10* | (2006.01) | |
| *A61M 16/04* | (2006.01) | |

(52) U.S. Cl.
USPC ............ 128/207.15; 128/202.27; 128/205.24; 128/205.27; 128/207.16; 128/912

(58) Field of Classification Search
USPC .................. 128/202.27, 207.14, 912, 200.26, 128/207.15–207.18, 205.12, 205.19, 205.24, 128/205.27, 200.24
See application file for complete search history.

(56) References Cited

U.S. PATENT DOCUMENTS

| | | | | |
|---|---|---|---|---|
| 4,022,219 | A | * | 5/1977 | Basta ........................ 128/207.14 |
| 4,506,665 | A | * | 3/1985 | Andrews et al. .......... 128/202.27 |
| 5,309,902 | A | * | 5/1994 | Kee et al. .................. 128/202.27 |
| 5,325,851 | A | * | 7/1994 | Reynolds et al. ........ 128/207.16 |
| 5,377,672 | A | * | 1/1995 | Kee ........................... 128/207.16 |
| 5,520,175 | A |   | 5/1996 | Fry |
| 5,791,337 | A | * | 8/1998 | Coles et al. .............. 128/200.26 |
| 6,254,591 | B1 | * | 7/2001 | Roberson ....................... 604/541 |
| 7,089,942 | B1 |   | 8/2006 | Grey |
| 7,293,561 | B2 |   | 11/2007 | Madsen et al. |
| 7,913,693 | B2 |   | 3/2011 | Nelson et al. |
| 8,186,349 | B2 |   | 5/2012 | Kusunoki et al. |
| 2007/0028925 | A1 | * | 2/2007 | Madsen et al. ........... 128/207.15 |
| 2007/0044806 | A1 | * | 3/2007 | Madsen et al. ........... 128/207.15 |
| 2007/0089748 | A1 |   | 4/2007 | Madsen et al. |
| 2008/0047562 | A1 |   | 2/2008 | Colburn et al. |
| 2008/0053454 | A1 | * | 3/2008 | Pasillas et al. ............ 128/207.15 |
| 2008/0110468 | A1 | * | 5/2008 | Nelson et al. ............. 128/207.15 |
| 2008/0121236 | A1 | * | 5/2008 | Field ......................... 128/207.15 |
| 2010/0113916 | A1 |   | 5/2010 | Kumar |
| 2010/0269830 | A1 |   | 10/2010 | Layer et al. |
| 2010/0307508 | A1 |   | 12/2010 | Li et al. |
| 2011/0237896 | A1 |   | 9/2011 | Black et al. |

* cited by examiner

*Primary Examiner* — Justine Yu
*Assistant Examiner* — Christopher Miller
(74) *Attorney, Agent, or Firm* — Baker & Hostetler LLP (57) ABSTRACT

The present invention provides in some embodiments, an endotracheal tube with subglottic secretion suction and a detachable suction line. The endotracheal tube is an elongate tube having an outer wall defining an elongate central lumen and an elongate suction lumen. An inflatable cuff is attached near a distal end of the elongate tube. The shoulder of the inflatable cuff is inverted in order to increase the diameter of the cuff from its distal end to its proximal end. The endotracheal tube also includes a connector to couple the suction lumen to a source of suction to remove subglottic secretions from the area above the cuff.

20 Claims, 12 Drawing Sheets

ENDOTRACHEAL TUBE WITH SUBGLOTTIC SECRETION SUCTION AND DETACHABLE SUCTION CONNECTION LINE

CROSS REFERENCE TO RELATED APPLICATION

This application claims priority to earlier filed U.S. Provisional Application No. 61/327,857, filed on Apr. 26, 2010, the disclosure of which is hereby incorporated by reference, in its entirety.

FIELD OF THE INVENTION

The present invention generally relates to an endotracheal tube. More particularly, the present invention pertains to an endotracheal tube with subglottic secretion suction and a detachable suction connection line.

BACKGROUND OF THE INVENTION

Endotracheal tubes are commonly used for airway management, mechanical ventilation, and as a drug delivery device when intravenous delivery cannot be established. An endotracheal tube is inserted through a process called intubation. During intubation, the endotracheal tube is inserted into the trachea through the patient's mouth, in order to keep the airway open and to allow air to reach the lungs. Endotracheal tubes often include a cuff to prevent air leaks during mechanical ventilation. This cuff is most commonly positioned at the distal end of the tube and can be inflatable.

Additionally, it is possible for undesirable subglottic secretions to collect around the top of the cuff. In order to prevent ventilator-associated pneumonia (VAP), it can be beneficial to remove these secretions by some means. One way to remove these secretions is to remove the endotracheal tube and then re-intubate the patient. However, continued re-intubation can be traumatic to the patient's trachea and is therefore not preferable. Alternatively, suction can be applied to remove these secretions through an additional lumen in the ET tube post intubation.

It is therefore desirable to provide a device and method for suctioning these subglottic secretions from the tracheal mucosa without having to remove the endotracheal tube.

SUMMARY OF THE INVENTION

The foregoing needs are met, to a great extent, by the present invention, wherein in some embodiments an endotracheal tube that is capable of overcoming the disadvantages described herein at least to some extent is provided.

In accordance with an embodiment of the present invention a connector to couple a suction lumen of an endotracheal tube to a source of suction includes a first connector component coupled to an opening in the suction lumen defined by an outer wall of the endotracheal tube. The connector also can include a second connector component having a first face configured to couple to the first connector component and having a second face configured to couple to a source of suction. The first connector component and the second connector component can be in fluid communication. Additionally, the first and second connector components can define a flow path for the suction of secretions from the suction lumen of the endotracheal tube.

In accordance with another embodiment of the present invention, The first connector can include a detent and the second connector can include a groove. The detent can then couple with the groove to lock the first connector to the second connector. The first connector component can also include an end cap. Additionally, the second face of the second connector component is coupled to a first end of a tube. The second end of the tube is coupled to a third connector component, which is configured to couple to a source of suction.

In accordance with another embodiment of the present invention, the connector assembly can include a flange that is configured to obstruct at least a portion of the suction lumen proximal to the suction lumen opening. The first and second connector components can be made from a plastic, resin, or any other suitable material. The first connector can include a detent and the second component can include a corresponding groove, such that the groove and the detent couple to lock the first and second connector together. The detent and groove can further be configured to provide an air tight seal between the first connector and the second connector.

In accordance with another embodiment of the present invention an endotracheal tube includes an elongate tube having an outer wall. The outer wall defines a generally cylindrical elongate central lumen and an elongate suction lumen. The endotracheal tube can also include an inflatable cuff attached near a distal end of the elongate tube. The inflatable cuff can include a proximal end and a distal end and an inner surface and an outer surface. A connector to couple the suction lumen of the endotracheal tube to a source of suction includes a first connector component coupled to an opening in the suction lumen defined by an outer wall of the endotracheal tube. The connector also can include a second connector component having a first face configured to couple to the first connector component and having a second face configured to couple to a source of suction. The first connector component and the second connector component can be in fluid communication. Additionally, the first and second connector components can define a flow path for the suction of secretions from the suction lumen of the endotracheal tube. The first connector can also define an opening for passage of fluid in communication with the suction lumen. The connector opening can be equal to or larger than a width of the suction lumen.

In accordance with another embodiment of the present invention The first connector can include a detent and the second connector can include a groove. The detent can then couple with the groove to lock the first connector to the second connector. The first connector component can also include an end cap. Additionally, the second face of the second connector component is coupled to a first end of a tube. The second end of the tube is coupled to a third connector component, which is configured to couple to a source of suction. The inner surface of the proximal end of the cuff is attached to the outer wall of the endotracheal tube and the outer surface of the distal end of the cuff is attached to the endotracheal tube.

In accordance with another embodiment of the present invention, the connector assembly can include a flange that is configured to obstruct at least a portion of the suction lumen proximal to the suction lumen opening. The first and second connector components can be made from a plastic, resin, or any other suitable material. The first connector can include a detent and the second component can include a corresponding groove, such that the groove and the detent couple to lock the first and second connector together. The detent and groove can further be configured to provide an air tight seal between the first connector and the second connector.

In accordance with yet another embodiment of the present invention, an endotracheal tube assembly includes an elongate tube having an outer wall defining an elongate central lumen, an elongate suction lumen, and a first and second suction lumen opening. An inflatable cuff can be attached near a distal end of the elongate tube just distal to the second suction lumen opening defined by the outer wall of the elongate tube. Additionally, a connector assembly can be included to couple the suction lumen of the endotracheal tube to a source of suction. The connector assembly can have a first end that couples to the first suction lumen opening. The first end can also define an opening for passage of fluid that is equal to or larger than a width of the first suction lumen opening and can be in communication with the suction lumen via the first suction lumen opening. The connector assembly can also have a second end that defines an opening in fluid communication with the opening defined by the first end of the connector assembly and the suction lumen. The second end can be configured to be connected to the source of suction.

In accordance with another embodiment of the present invention, the first end of the connector can include a flange that is configured to obstruct at least a portion of the suction lumen proximal to the first suction lumen opening. The connector assembly can be configured to provide an unobstructed fluid flow path from the suction lumen to the source of suction. Additionally, the connector assembly can be configured to provide an air tight seal between the suction lumen and the source of suction.

There has thus been outlined, rather broadly, certain embodiments of the invention in order that the detailed description thereof, herein may be better understood, and in order that the present contribution to the art may be better appreciated. There are, of course, additional embodiments of the invention that will be described below as part of the disclosure.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the disclosure be regarded as including such equivalent constructions insofar as they do not depart from the spirit and scope of the present invention.

DETAILED DESCRIPTION

The present invention provides in some embodiments, an endotracheal tube with subglottic secretion suction and a detachable suction line. The endotracheal tube is an elongate tube having an outer wall defining an elongate central lumen and an elongate suction lumen. An inflatable cuff is attached near a distal end of the elongate tube. The endotracheal tube also includes a connector to couple the suction lumen to a source of suction to remove subglottic secretions from the area above the cuff.

Figure 1:
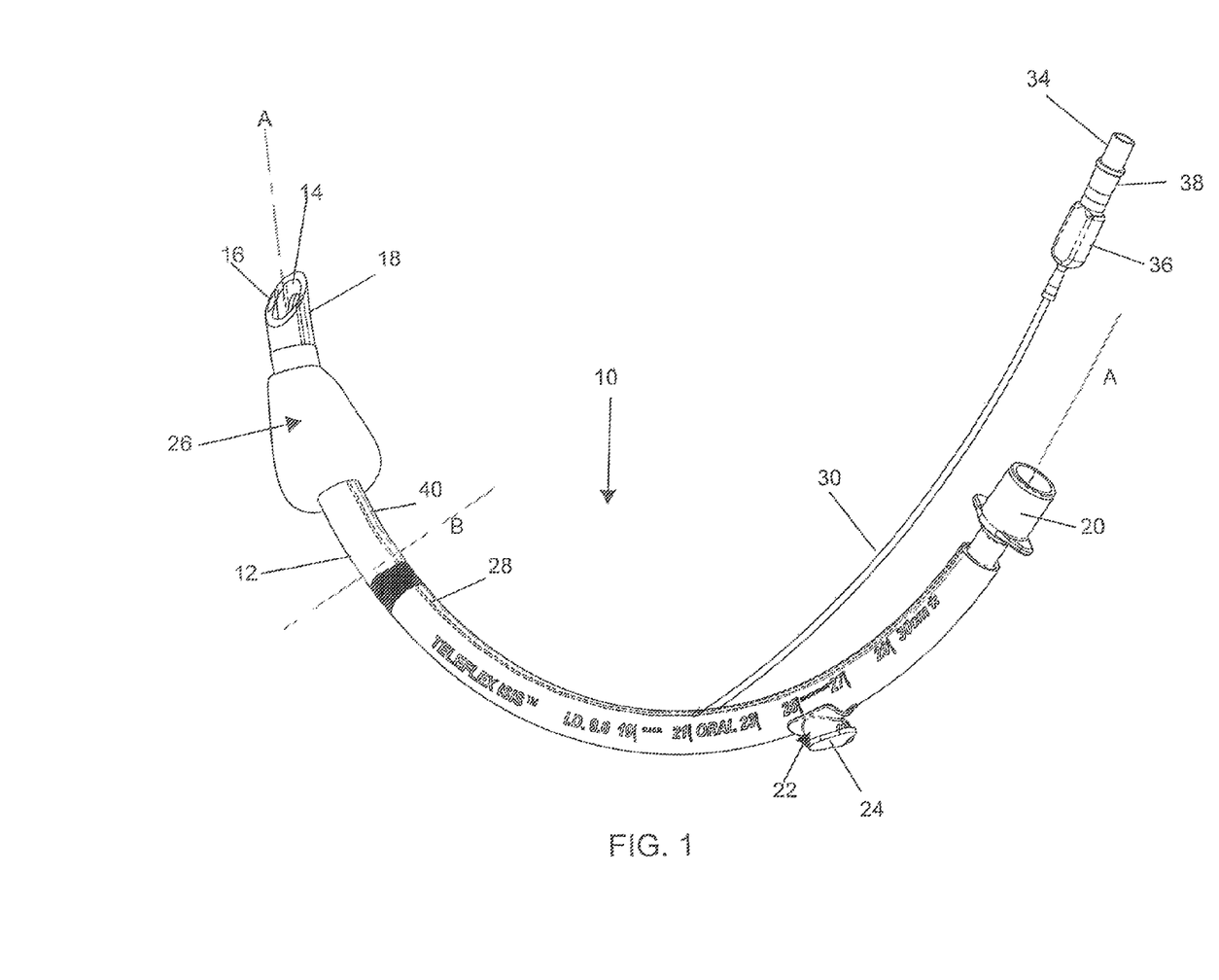
FIG. 1 illustrates a side view of an endotracheal tube in accordance with an embodiment of the invention.

The invention will now be described with reference to the drawing figures, in which like reference numerals refer to like parts throughout. FIG. 1 illustrates an endotracheal tube 10 in accordance with the invention. The endotracheal tube 10 includes an outer wall 12 which defines a generally cylindrical central lumen 14. The outer wall 12 also defines an elongate suction lumen 16. The endotracheal tube 10 has a longitudinal axis 'A' extending through the length of the tube 10 and one or more latitudinal axis 'B' extending across the tube 10. The endotracheal tube has a distal end 18, which is inserted into the patient's trachea during the intubation procedure, and a proximal end 20, which is coupled to the respirator or other source of air for the patient. The endotracheal tube 10 can also include a connector 22 mounted on the outer wall 12 of the endotracheal tube. As shown in FIG. 1, the connector can also include a cover 24 shown in a closed position in FIG. 1.

FIG. 1 also illustrates an inflation cuff 26 positioned proximate to the distal end 18 of the endotracheal tube 10. The inflation cuff 26 can be inflated via an inflation lumen 28 defined by the outer wall 12 of the endotracheal tube 10. As shown in FIG. 1, an inflation tube 30 extends from the inflation lumen 28. A distal end of the inflation tube 30 is inserted into the inflation lumen 28 and a proximal end 34 can be coupled to a source of air for inflation. A pilot 36 and a valve 38 can be coupled to the proximal end 34 of the inflation tube in order to keep air in the cuff 26, once it is inflated. The endotracheal tube 10 can also include an x-ray opaque stripe 40 extending through the outer wall 12 of the endotracheal tube 10, so that proper placement of the tube 10 can be confirmed via x-ray, if necessary.

Figure 2:
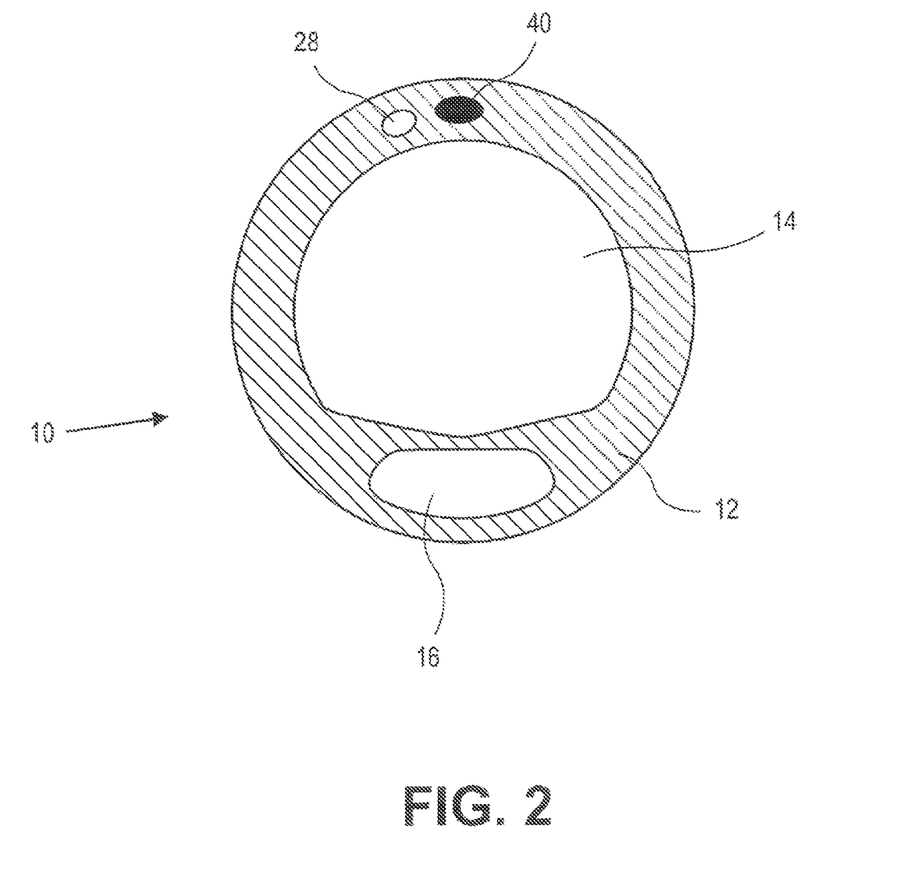
FIG. 2 illustrates a sectional view along axis 'B' of the endotracheal tube shown in FIG. 1.

FIG. 2 illustrates a sectional view of an endotracheal tube taken along axis 'B' illustrated in FIG. 1. As illustrated in FIG. 2, the endotracheal tube 10 includes a central lumen 14, a suction lumen 16, an inflation lumen 28 defined by the outer wall 12 of the endotracheal tube 10. The x-ray opaque stripe 40 also extends through the outer wall 12 of the tube 10. The central lumen 14 is shown as generally circular in cross-sectional shape, while the suction lumen 16 is shown as generally elliptical in cross-sectional shape. However, the central lumen 14 and the suction lumen 16 can take any shape which allows for the passage of air or secretions. Additionally, the endotracheal tube 10 can be formed from polyvinyl chloride or any other suitable material for forming an endotracheal tube.

Figure 3:
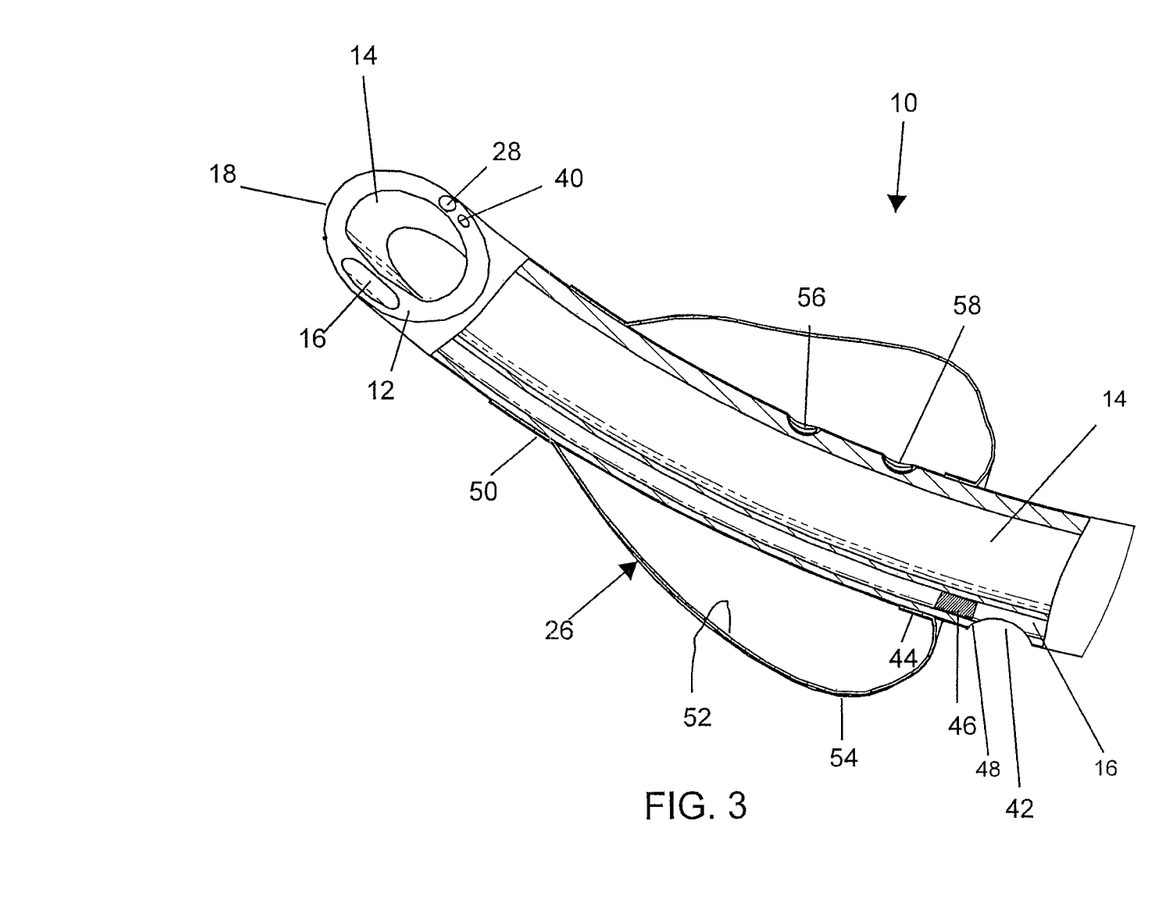
FIG. 3 illustrates a partially sectional view along axis 'A' of the endotracheal tube shown in FIG. 1.

FIG. 3 illustrates a partial sectional view of the endotracheal tube and inflation lumen taken along axis 'A,' illustrated in FIG. 1. FIG. 3 shows the suction lumen 16 extending through the length of the endotracheal tube 10. The outer wall 12 of the endotracheal tube 10 defines a suction lumen first opening 42 in the suction lumen 16, just proximal of a proximal end 44 of the inflation cuff 26. A plug 46 can be positioned in the suction lumen 16 just distal to a distal end 48 of the suction lumen first opening 42. The plug 46 can be formed from UV glue or any other suitable material for sealing off the portion of the suction lumen 16 distal to the distal end 48 of the suction lumen first opening 42. In this way, the suction lumen 16 effectively terminates at the suction lumen first opening 42, where secretions accumulating around the proximal end of cuff 26 can be suctioned.

FIG. 3 also illustrates the inflation cuff 26. The cuff can include a distal end 50 and a proximal end 44, as well as an inner surface 52 and an outer surface 54. The inner surface 52 of the distal end 50 of the cuff 26 is bonded to the endotracheal tube 10 near its distal end 18. Preferably, the proximal end 44 of the cuff 26 can be folded in, or inverted, such that the outer surface 54 is bonded to the endotracheal tube 10. The bond can be formed by a suitable adhesive, melting, or any other form of bond that will connect the cuff 26 to the tube 10. Inverting the proximal end 44 of the cuff 26, but not the distal end 50, allows for the cuff 26 to increase in diameter from its distal end 50 to its proximal end 44. Additionally, the outer wall 12 of the endotracheal tube 10 defines an inflation lumen first opening 56 and an inflation lumen second opening 58 to allow fluid communication between the inflation lumen 28 and the inflation cuff 26.

Figure 4:
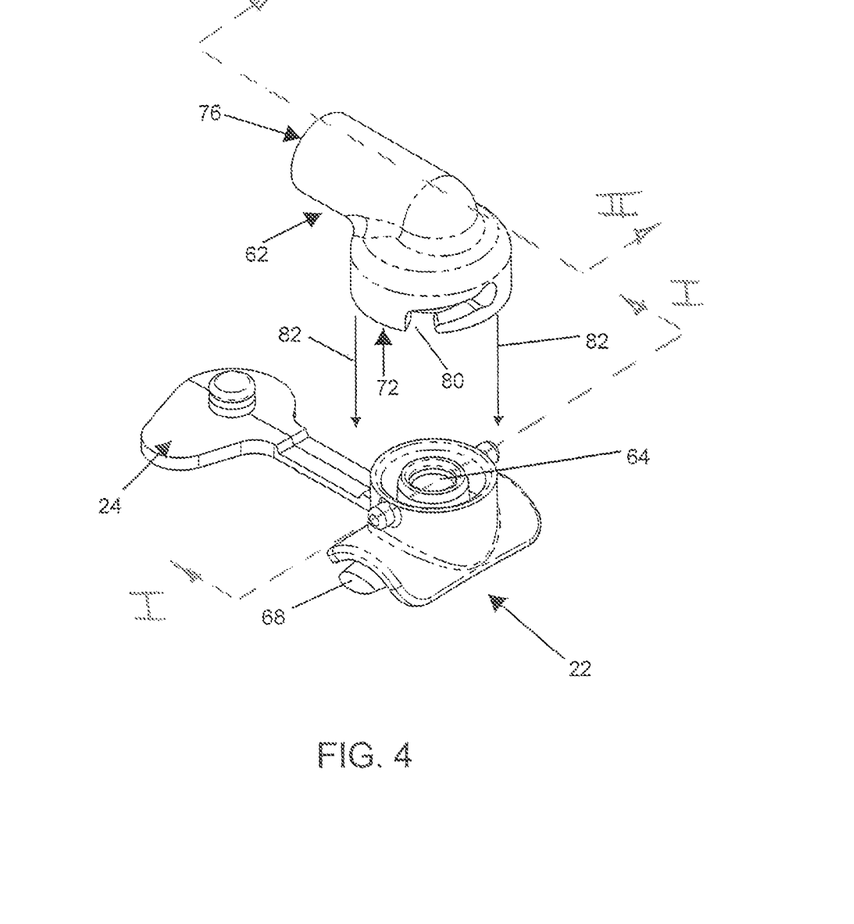
FIG. 4 illustrates ends of a connector assembly for a detachable suction connection line for an endotracheal tube in accordance with an embodiment of the invention.
Figure 5:
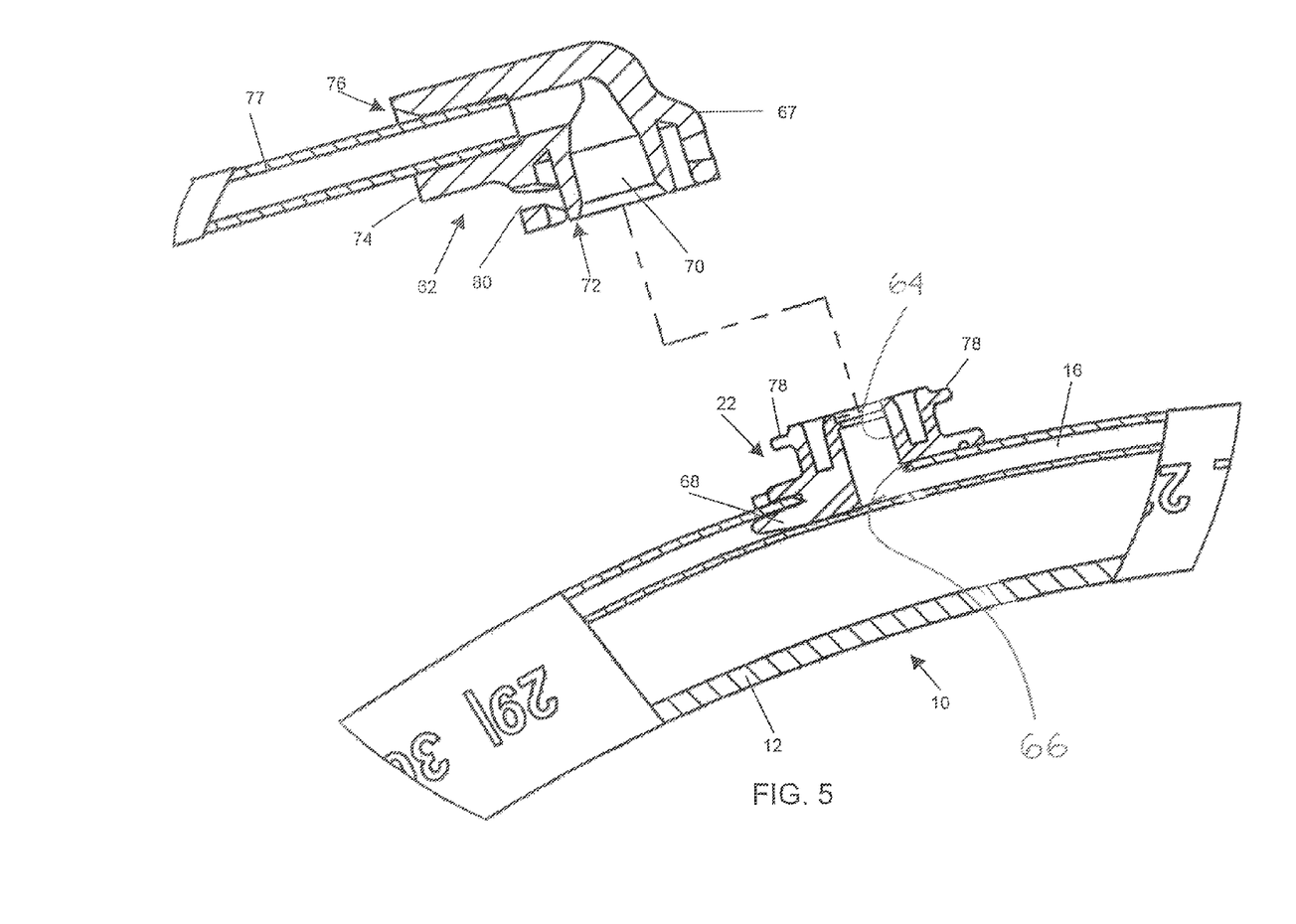
FIG. 5 illustrates a sectional view of the connector assembly along section line I-I and section line II-II for the detachable suction connection line for an endotracheal tube.

FIGS. 4 and 5 illustrate ends of a connector assembly including a connector 22 and the detachable suction connection line 62 for an endotracheal tube 10 in accordance with an embodiment of the invention. The connector 22 on tube 10 defines a connector opening 64 which extends into the suction lumen 16 through suction lumen second opening 66 defined by the outer wall 12 of the endotracheal tube 10. The connector opening 64 on connector 22 is, as wide or, preferably, wider than the suction lumen 16 to allow for unobstructed suctioning, when the connector 22 is attached. The invention thereby provides for a way to suction secretions from the subglottic space proximal to the inflation cuff, through a lumen to an ultimate suction source, where the suction pathway from the patient end starting at the suction lumen first opening 42 does not contract or narrow to impede suctioning all the way through the endotracheal tube 10 and out of the device. The connector 22 can also include a flange 68 which blocks off the portion of the suction lumen 16 proximal to the suction lumen second opening 66. A distal end 67 of the detachable suction connection line 62, also defines a first opening 70 on a first face 72 and a second opening 74 on a second face 76, such that an elongate tube 77 of the detachable suction line 62 inserted into second opening 74 is in fluid communication with the suction lumen 16 when the suction connection line 62 is coupled to connector 22, as described further below. The detachable suction line 62 can be coupled to the connector 22 with a detent locking mechanism or any other suitable means of connection, and is designed to create an air tight seal when connected. As illustrated in the embodiment of FIGS. 4 and 5, the connector 22 includes detents 78 and the detachable suction line includes grooves 80 to form the detent locking mechanism. The connector 22 can also include a cover 24 shown in the open position in FIG. 4.

Figure 6:
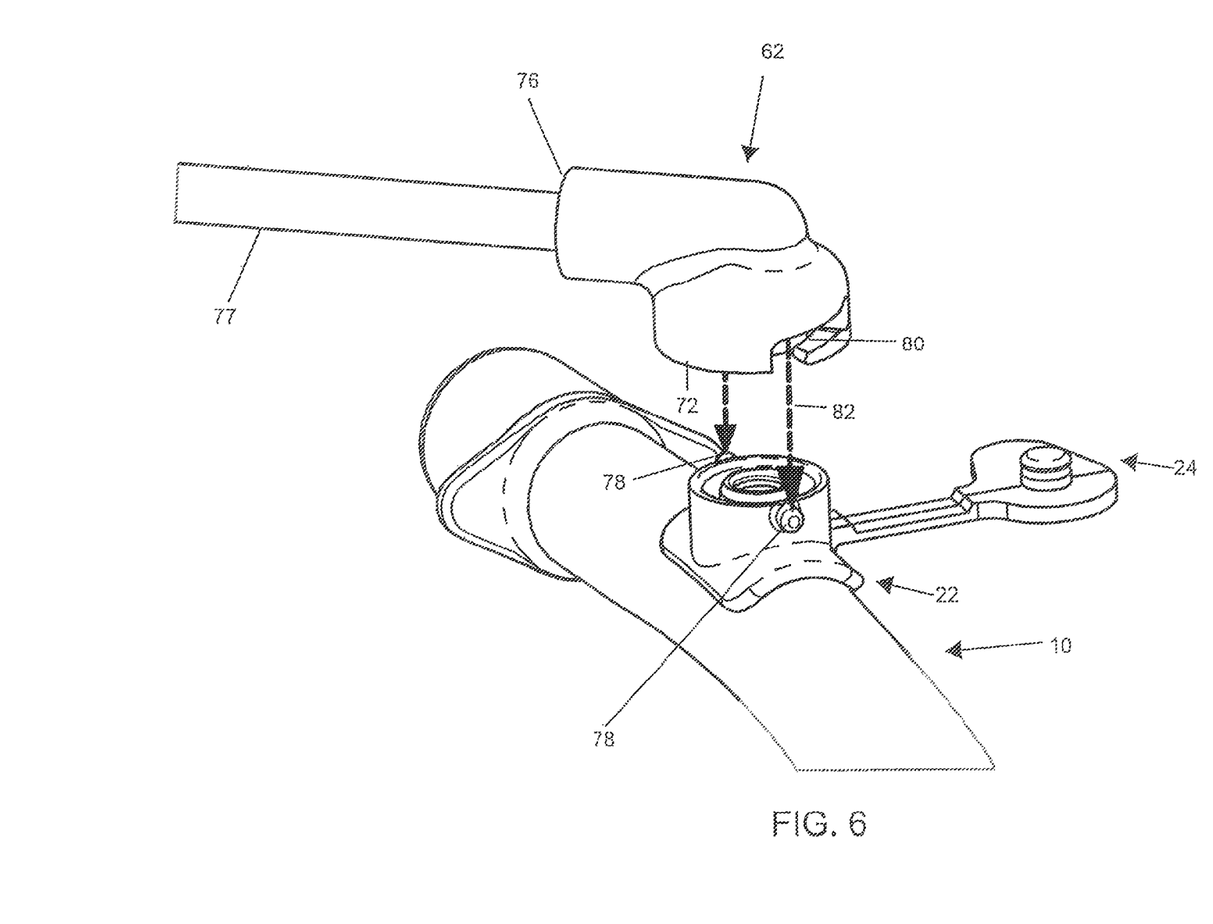
FIG. 6 illustrates another view of ends of a connector assembly for a detachable suction connection line for an endotracheal tube in accordance with an embodiment of the invention.
Figure 7:
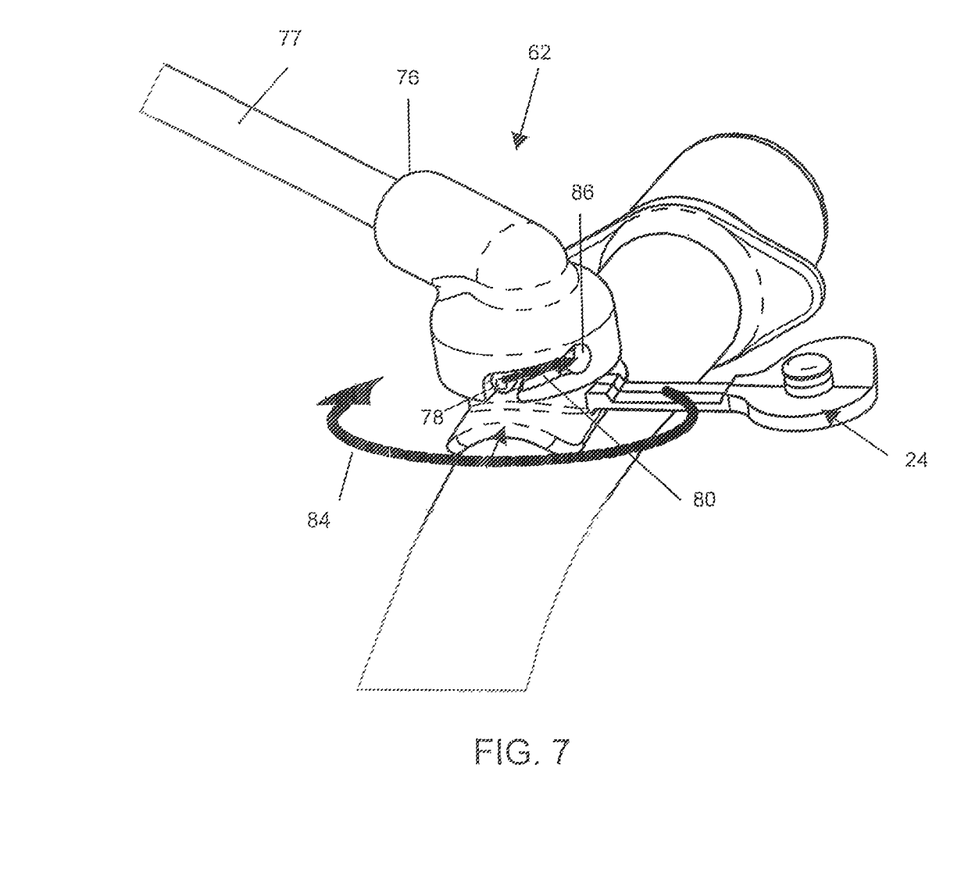
FIG. 7 illustrates a view of the ends of a connector assembly for a detachable suction connection line for an endotracheal tube in a first coupled position, in accordance with an embodiment of the invention.
Figure 8:
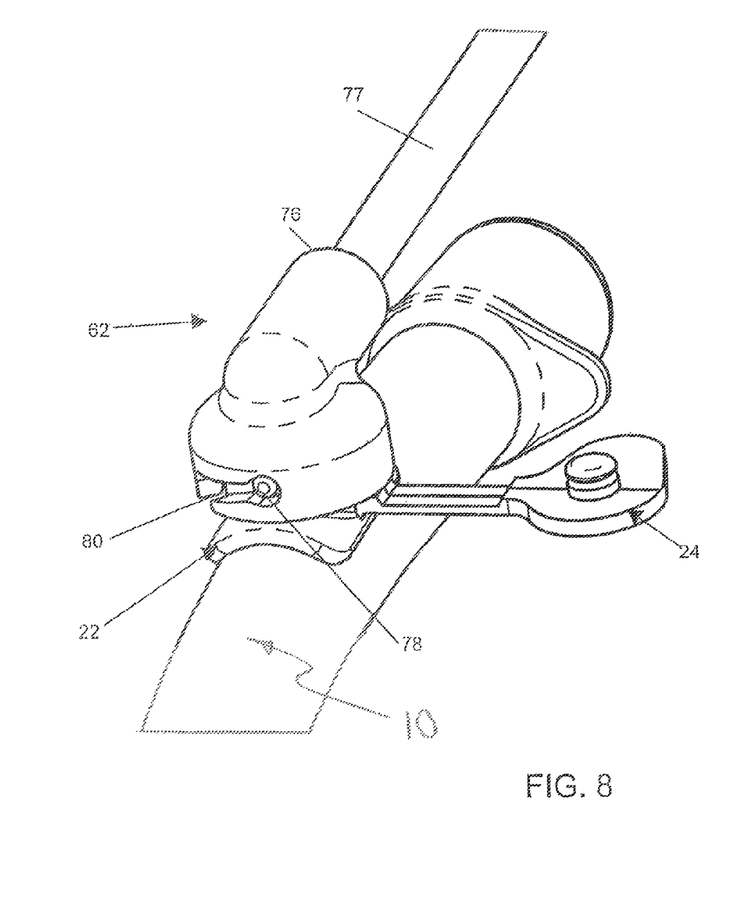
FIG. 8 illustrates ends of a connector assembly for a detachable suction connection line for an endotracheal tube in a second coupled position, in accordance with an embodiment of the invention.
Figure 9:
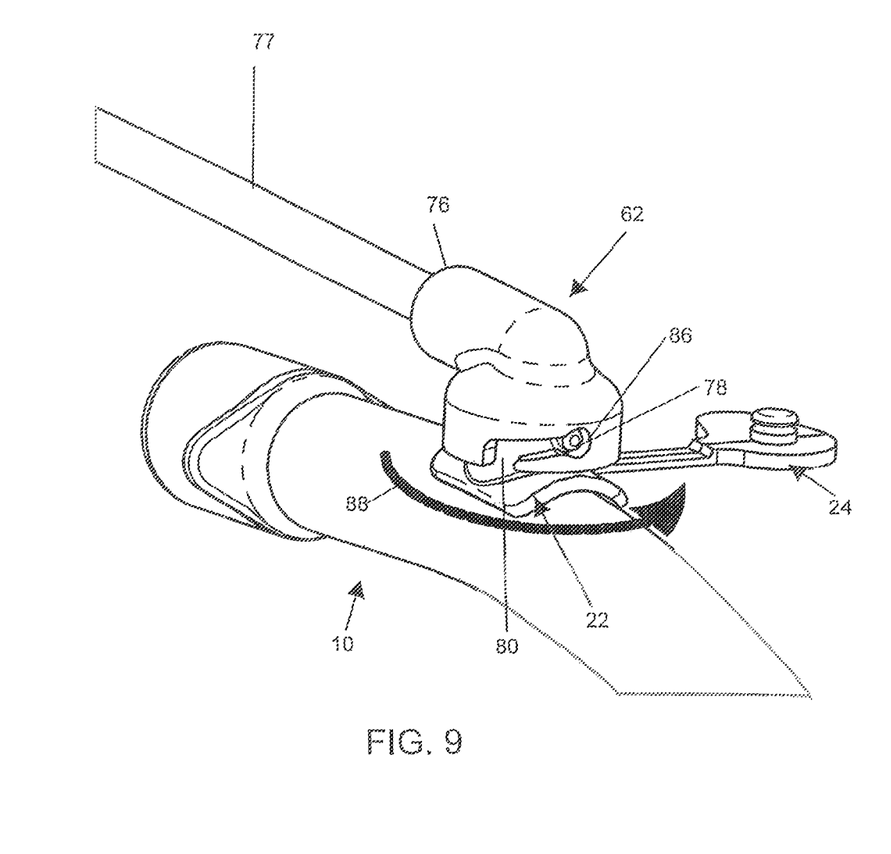
FIG. 9 illustrates another view of the coupled ends of a connector assembly for a detachable suction connection line for an endotracheal tube in accordance with an embodiment of the invention, as shown in FIG. 8.

FIGS. 6, 7, 8 and 9 illustrate the coupling of a connector 22 and the detachable suction connection line 62 for an endotracheal tube 10 in accordance with an embodiment of the invention. As shown in FIG. 6, the grooves 80 are lined up with the detents 78 and the detachable suction connection line 62 is lowered onto the connector 22 in the direction of arrows 82. As shown in FIG. 7, the detachable suction connection line 62 is then turned in the direction of arrow 84, so that the detents 78 slide through grooves 80 and into the notch 86, as shown in FIG. 8. To remove the detachable suction line 62 it is turned in the direction of arrow 88, as shown in FIG. 9. Additionally, the connector 22 can include the cover 24, shown in its open position in FIGS. 6, 7, 8, and 9. The cover 24 can be used to cover the connector 22 when suction is not in use.

Figure 10:
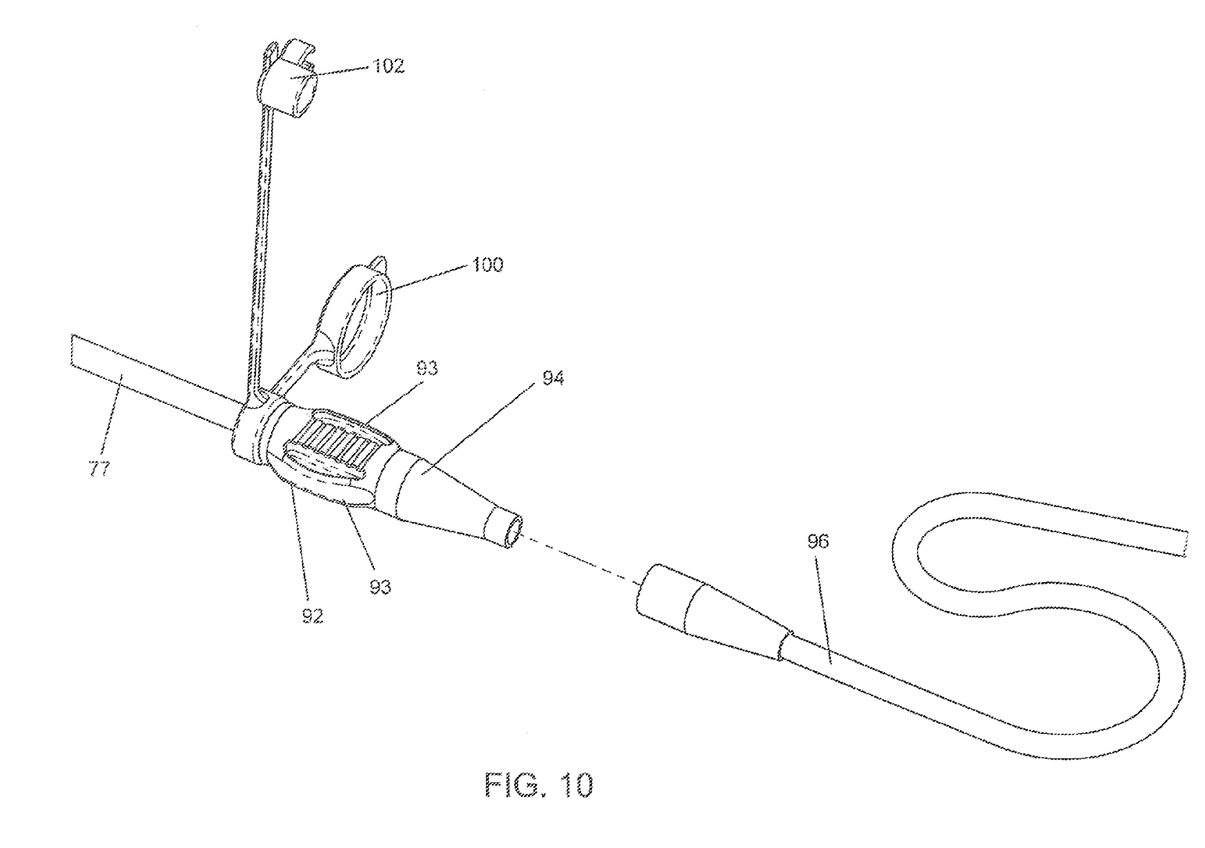
FIG. 10 illustrates a proximal end of a suction connection line for an endotracheal tube in accordance with an embodiment of the invention.
Figure 11:
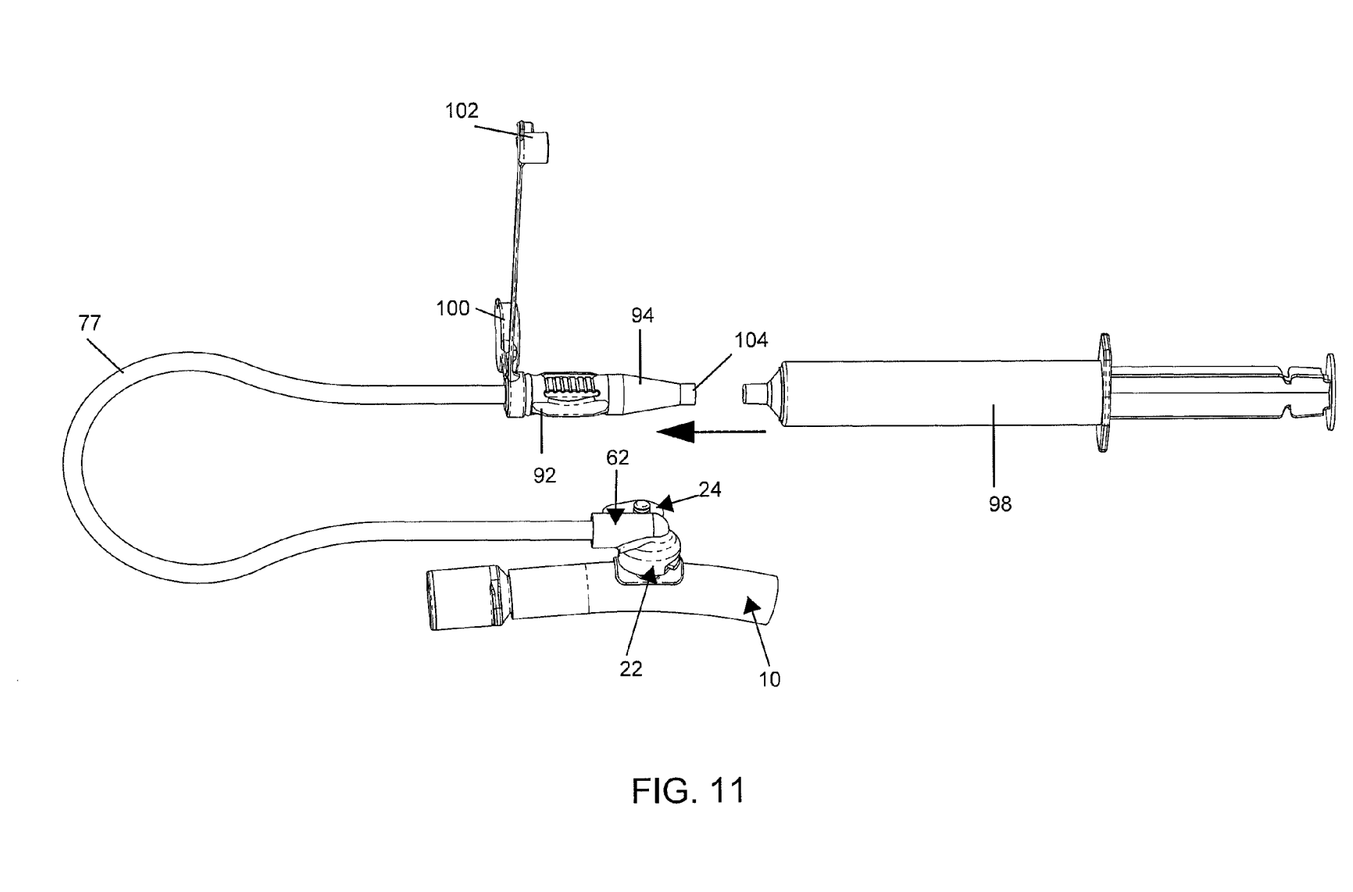
FIG. 11 illustrates a suction connection line coupled to an endotracheal tube in accordance with an embodiment of the invention.

FIGS. 10 and 11 illustrate a proximal end 92 of a suction connection line 62 for an endotracheal tube 10 in accordance with an embodiment of the invention. The proximal end 92 of the suction connection line 62 includes a coupler 94 to couple the suction connection line 62 to a source of suction. As shown in FIG. 10, the coupler 94 can be connected to a suction line 96 from a suction unit. Alternately, as shown in FIG. 11 the coupler 94 can be connected to a suction syringe 98. Proximal end 92 can have a flattened shape defining lateral extensions 93 for allowing enhanced gripping to connect and disconnect to external suction source line 96.

Figure 12:
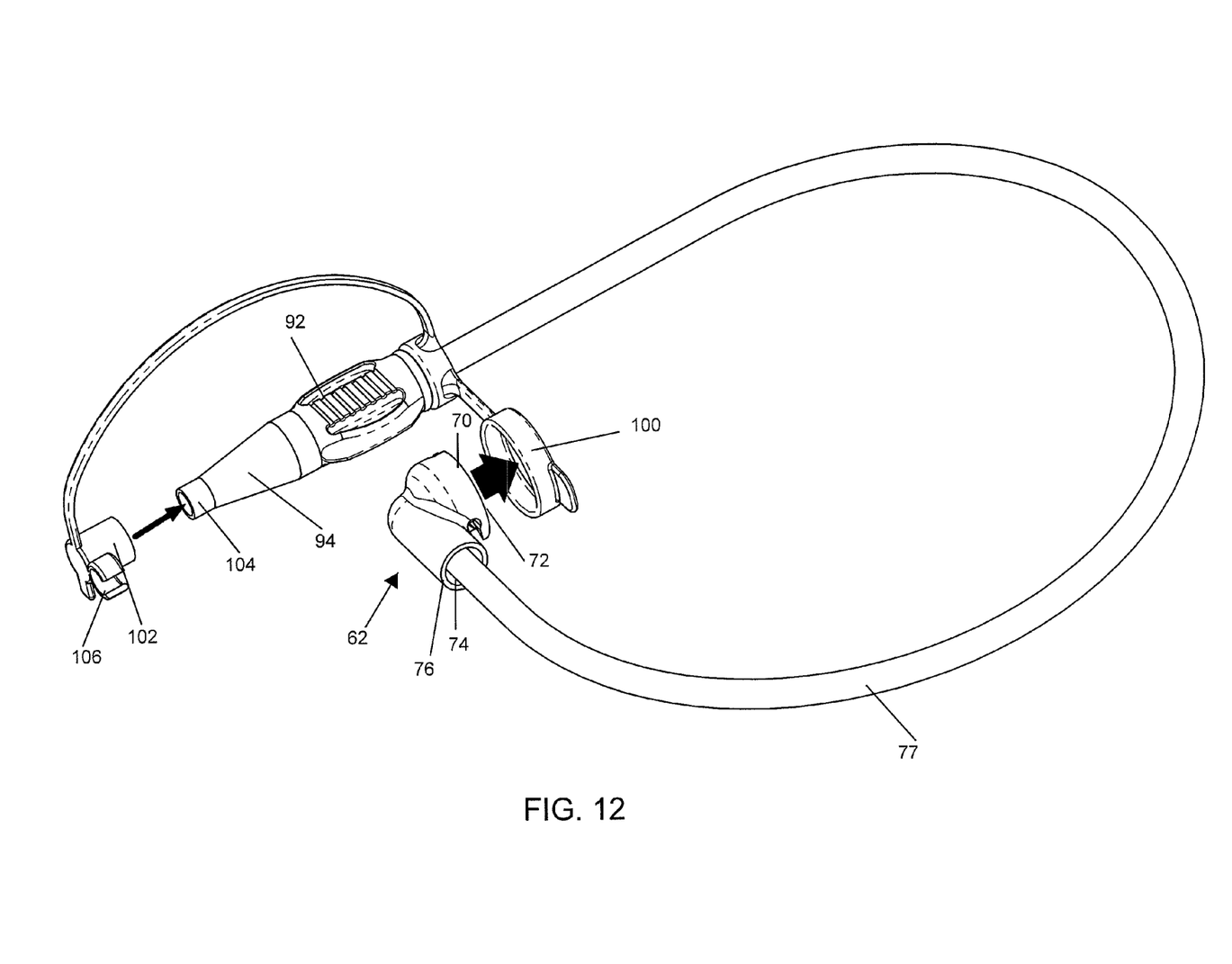
FIG. 12 illustrates another view of a suction connection line for an endotracheal tube in accordance with an embodiment of the invention.

FIG. 12 illustrates a proximal end 92 of a suction connection line 62 for an endotracheal tube 10 in accordance with an embodiment of the invention. The coupler 94 can also include a suction line end cap 100 and a coupler en cap 102. The suction line end cap 100 can be used to cover the distal end 67 of the suction connection line 62. The coupler end cap 102 can be used to cover a proximal end 104 of the coupler 94. When not in use the coupler end cap 102 also can include a clip 106 to connect the coupler end cap 102 to the elongate tube 77 of the suction connection line 62.

In one embodiment, the invention provides the ability to attach and detach a suction line to a standard endotracheal tube allowing the tube to be used as either a standard tube or as a subglottic secretion suction tube. The detachable suction line has been designed with a detent locking device for ease of connection and to reduce accidental disconnection. This reduces suction line restrictions, improving the suctioning rate of the subglottic secretions that normally pool above the cuff.

An embodiment of the invention modifies the standard endotracheal tube by adding the dorsal suction lumen and a sealable connection port thereto. The inflation cuff can be modified by inverting the top sleeve of the cuff when bonding to the tube, and is intended to decrease the space between the top of the cuff and the suction port for more efficient subglottic suctioning.

The parts utilized can consist of a conventional PVC tube with the various connectors made of common resins. The injection molded plastic connectors are designed with a detent locking mechanism that is used for the suction accessory line. The suction lumen line is typically bonded into the suction lumen which restricts the inner diameter (ID) of the tube. Thus, the suction tube ID is not restricted thus improving the suction capability. The interference between the suction lumen and the suction line is minimized with the interlocking systems, reducing the restrictions to the flow of secretions and making the device less prone for occlusions.

In one embodiment, the male connector is preferably placed at a dorsal side of the endotracheal tube centered with the upper opening of the suction lumen. It is preferred to be located above the 24 cm mark which prevents the male connector having contact with the mouth or teeth when the Endotracheal tube is in place. The suction line accessory has the female connector that is packaged separately and attach to the endotracheal tube male connector.

The design allows the attachment and detachment of the suction line connector from a standard endotracheal tube allowing the tube to be used as either a standard tube or as a subglottic secretion suction tube. This allows for subglottic secretion removal without re-intubation. The design features a connector with a sealing cap, permanently attached to the dorsal lumen, which can be opened and used with a separately packaged suction line with mating connector. The design of the tube port and extension line connectors improve the suction function through the endotracheal tube suction lumen by maintaining a constant lumen geometry, thus reducing the restriction to the flow of secretions.

The subject invention improves patient safety by providing the ability to attach the suction accessory line separately. This allows the use of a standard endotracheal tube across all patient populations and provide for subglottic secretion removal only where necessary without re-intubation. A classic example would be the patient that goes into surgery intubated with a standard ET tube, and subsequently requires unanticipated subglottic secretion removal. Currently this would require the patient to be extubated and re-intubated with an ET tube having a suction lumen. Clinical practice discourages extubating the patient except in the most serious cases due to the hazards involved with re-intubation which include but are not limited to increase risk of infection, loss of airway, and tracheal trauma The subject invention makes the subglottic suctioning more efficient. The male connector is attached to the upper opening of the dorsal lumen; and does not occlude or restrict the suction lumen as is evident with the competitor's design. The fluids and secretions are removed with less suctioning vacuum pressure which reduces the potential for tracheal hematomas. This will provide a cost-effective standard Endotracheal tube and a suction line accessory that can be used as is needed during any procedure.

The many features and advantages of the invention are apparent from the detailed specification, and thus, the disclosure is intended to cover all such features and advantages of the invention which fall within the true spirit and scope of the invention. Further, because numerous modifications and variations will readily occur to those skilled in the art, it is not desired to limit the invention to the exact construction and operation illustrated and described, and accordingly, all suitable modifications and equivalents may be resorted to falling within the scope of the invention.

What is claimed is:

1. A connector assembly coupled to a suction lumen of an endotracheal tube, the connector assembly comprising:
a first connector component coupled to an opening in the suction lumen, the opening in the suction lumen defined by an outer wall of the endotracheal tube, the first connector component being distinct from the endotracheal tube; and
a second connector component having a first face configured to couple to the first connector component and having a second face configured to couple to a source of suction,
wherein the first connector component and the second connector component are in fluid communication and define a closed flow path for drawing secretions from the suction lumen of the endotracheal tube, and
wherein the first connector component includes a flange that extends radially into the suction lumen, the flange being configured to seal the suction lumen against passing a flow through the suction lumen in a longitudinal direction.

2. The connector assembly of claim 1, wherein a substantially radial face of the flange extends into the suction lumen proximal to the suction lumen opening.

3. The connector assembly of claim 1, wherein the first connector component comprises an end cap.

4. The connector assembly of claim 1, wherein the second face of the second connector component is coupled to a first end of a tube and wherein a second end of the tube is coupled to a third connector component configured to couple to the source of suction.

5. The connector assembly of claim 1, wherein the first connector component defines an opening in the first connector component for passage of fluid in communication with the suction lumen, and
wherein a dimension of the opening in the first connector component is equal to or larger than a width of the suction lumen.

6. The connector assembly of claim 1, wherein the first connector component and the second connector component are formed from a plastic.

7. The connector assembly of claim 1, wherein the first connector component comprises a detent and the second connector component comprising a groove such that the detent couples with the groove to lock the first connector component to the second connector component.

8. The connector assembly of claim 7, wherein the detent and the groove are configured to provide an air tight seal between the first connector component to the second connector component.

9. An endotracheal tube assembly comprising:
an elongate tube having an outer wall, the outer wall defining a generally cylindrical elongate central lumen and also defining an elongate suction lumen;
an inflatable cuff attached near a distal end of the elongate tube wherein the inflatable cuff has a proximal end and a distal end and an inner surface and an outer surface; and
a connector assembly to couple the elongate suction lumen of the elongate tube to a source of suction, the connector assembly comprising:
a first connector component coupled to an opening in the elongate suction lumen defined by an outer wall of the elongate tube, the first connector component being distinct from the elongate tube; and
a second connector component having a first face configured to couple to the first connector component and having a second face configured to couple to the source of suction,
wherein the first connector component and the second connector component are in fluid communication and define a closed flow path for drawing secretions from the elongate suction lumen of the elongate tube, wherein the first connector component defines an opening for passage of fluid in communication with the elongate suction lumen, and wherein the first connector component includes a flange that extends radially into the suction lumen, the flange being configured to seal the suction lumen against passing a flow through the suction lumen in a longitudinal direction.

10. The endotracheal tube assembly of claim 9, wherein the first connector component and the second connector component are formed from a plastic.

11. The endotracheal tube assembly of claim 9, wherein the first connector component comprises an end cap.

12. The endotracheal tube assembly of claim 9, wherein the second face of the second connector component is coupled to a first end of a tube and wherein a second end of the tube is coupled to a third connector component configured to couple to the source of suction.

13. The endotracheal tube assembly of claim 9, wherein the inner surface of the distal end of the inflatable cuff is attached to the outer wall of the elongate tube, and the outer surface of the proximal end of the inflatable cuff is attached to the elongate tube.

14. The endotracheal tube assembly of claim 9, wherein a dimension of the opening of the first connector component is equal to or larger than a width of the elongate suction lumen.

15. The endotracheal tube assembly of claim 9, wherein the first connector component comprises a detent and the second connector component comprises a groove such that the detent couples with the groove to lock the first connector component to the second connector component.

16. The endotracheal tube assembly of claim 15, wherein the detent and groove are configured to provide an air tight seal between the first connector component and the second connector component.

17. An endotracheal tube assembly comprising:
an elongate tube having an outer wall, the outer wall defining
an elongate central lumen,
an elongate suction lumen,
a first opening of the elongate suction lumen, and
a second opening of the elongate suction lumen;
an inflatable cuff attached near a distal end of the elongate tube just proximal to the second opening of the elongate suction lumen; and
a connector assembly to couple the elongate suction lumen of the elongate tube to a source of suction, the connector assembly having a first end that couples to the first opening of the elongate suction lumen, the connector assembly including
a first connector component coupled to the first opening of the elongate suction lumen, the first connector component being distinct from the endotracheal tube, and
a second connector component having a first face configured to couple to the first connector component and having a second face configured to couple to the source of suction,
wherein the first connector component includes a flange that extends radially into the suction lumen, the flange being configured to seal the suction lumen against passing a flow through the suction lumen in a longitudinal direction.

18. The endotracheal tube assembly of claim 17, wherein the first end of the connector assembly also defines an opening in the first end of the connector assembly for passage of fluid,
wherein the opening in the first end of the connector assembly has a dimension that is equal to or larger than a width of the first opening of the elongate suction lumen,
wherein the opening in the first end of the connector assembly is in communication with the elongate suction lumen via the first opening of the elongate suction lumen, and
wherein the connector assembly has a second end that defines an opening in the second end of the connector assembly that is in fluid communication with the elongate suction lumen via the opening in the first end of the connector assembly, the second end of the connector assembly being configured to be connected to the source of suction.

19. The endotracheal tube assembly of claim 17, wherein the connector assembly is configured to provide an unobstructed fluid flow path from the elongate suction lumen to the source of suction.

20. The endotracheal tube assembly of claim 17, wherein the connector assembly is configured to provide an air tight seal between the elongate suction lumen and the source of suction.

* * * * *